US008350046B2

(12) United States Patent
Reichert et al.

(10) Patent No.: US 8,350,046 B2
(45) Date of Patent: Jan. 8, 2013

(54) METHOD FOR MANUFACTURING ARYL CARBOXAMIDES

(75) Inventors: Wolfgang Reichert, Frankenthal (DE); Christopher Koradin, Ludwigshafen (DE); Sebastian Peer Smidt, Offersheim (DE); Volker Maywald, Ludwigshafen (DE); Bernd Wolf, Fussgoenheim (DE); Michael Rack, Eppelheim (DE); Thomas Zierke, Boehl-Iggelheim (DE); Michael Keil, Freinsheim (DE)

(73) Assignee: BASF SE, Ludwigshafen (DE)

( * ) Notice: Subject to any disclaimer, the term of this patent is extended or adjusted under 35 U.S.C. 154(b) by 161 days.

(21) Appl. No.: 12/990,892

(22) PCT Filed: May 6, 2009

(86) PCT No.: PCT/EP2009/055446
§ 371 (c)(1),
(2), (4) Date: Nov. 3, 2010

(87) PCT Pub. No.: WO2009/135860
PCT Pub. Date: Nov. 12, 2009

(65) Prior Publication Data
US 2011/0054183 A1 Mar. 3, 2011

(30) Foreign Application Priority Data
May 8, 2008 (EP) .................. 08155888

(51) Int. Cl.
*C07D 213/82* (2006.01)
*C07D 231/14* (2006.01)
(52) U.S. Cl. .................. 546/316; 548/374.1
(58) Field of Classification Search .......... None
See application file for complete search history.

(56) References Cited

U.S. PATENT DOCUMENTS

| 5,618,951 | A | 4/1997 | Britton |
| 7,994,207 | B2 | 8/2011 | Zierke et al. |
| 2006/0276656 | A1 | 12/2006 | Lantzsch et al. |
| 2008/0015244 | A1 | 1/2008 | Dunkel et al. |
| 2008/0108686 | A1 | 5/2008 | Gewehr et al. |
| 2010/0022782 | A1 | 1/2010 | Zierke et al. |
| 2010/0069646 | A1 | 3/2010 | Sukopp et al. |

FOREIGN PATENT DOCUMENTS

| EP | 0 657 438 | 6/1995 |
| JP | 1975/49217 | 5/1975 |
| JP | 2001 172276 | 6/2001 |
| WO | WO 92/12970 | 8/1992 |
| WO | WO 93/11117 | 6/1993 |
| WO | WO 03/070705 | 8/2003 |
| WO | WO 2005/021532 | 3/2005 |
| WO | WO 2005/044804 | 5/2005 |
| WO | WO 2005/054244 | 6/2005 |
| WO | WO 2005/123690 | 12/2005 |
| WO | WO 2007/003540 | 1/2007 |
| WO | WO 2007/031323 | 3/2007 |
| WO | WO 2008/053043 | 5/2008 |
| WO | WO 2008/077907 | 7/2008 |

OTHER PUBLICATIONS

International Search Report for International Application No. PCT/EP2009/055446, filed May 6, 2009.
International Preliminary Report on Patentability for International Application No. PCT/EP2009/055446, filed May 6, 2009.
Asinger, F., "Uber die Verseifung substituierter Benzanilide", Journal fur Praktischer Chemie, (1935) 142, 291-300.
Bukhtiarova, T.A., et al., "Structure and Antiinflammatory Activity of Isonicotinic and Nicotinic Amides", Pharmaceutical Chem. Journal, (1997) 31, 597-599.
Cativiela, C., et al., "A Convenient Synthesis of N-Aryl-1,2-dihydro-2-oxo-3-pyridinecarboxamides, N-Aryl-N-methyl-1,2-dihydro-2-oxo-3-pyridinecarboxamides and Their 1-Methyl (O-Methyl)-Derivatives", Journal of Heterocyclic Chemistry, (1982) 19, 1093-1097.
Ettmayer, P., et al., "Solid-Phase Synthesis of 7-Acylamino-1,4-benzodiazepine-2,5-diones", J. Comb. Chem., (2003) 5, 253-259.
Kadesch, G., "Substituted Amides of 2,4,6-Trimethylbenzoic Acid", Journal of the American Chemical Society, (1942) 64, p. 726.

(Continued)

*Primary Examiner* — Kamal Saeed
(74) *Attorney, Agent, or Firm* — Brinks Hofer Gilson & Lione

(57) ABSTRACT

A process for preparing arylcarboxamides of the formula (I)

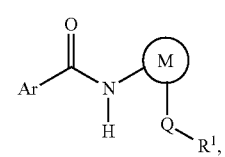

(I)

where
Ar = a mono- to trisubstituted phenyl, pyridyl or pyrazolyl ring, where the substituents are selected from halogen, $C_1$-$C_4$-alkyl and $C_1$-$C_4$-haloalkyl;
M = thienyl or phenyl, which may bear a halogen substituent;
Q = direct bond, cyclopropylene, fused bicyclo[2.2.1]heptane or bicyclo[2.2.1]heptene ring;
$R^1$ = hydrogen, halogen, $C_1$-$C_6$-alkyl, $C_1$-$C_4$-alkoxy, $C_1$-$C_4$-haloalkoxy, mono- to trisubstituted phenyl, where the substituents are selected from halogen and trifluoromethylthio, or cyclopropyl;
by reacting an acid chloride of the formula (II)

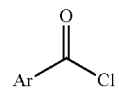

(II)

with an arylamine (III)

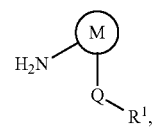

(III)

in a suitable nonaqueous solvent, wherein, in the absence of an auxiliary base,
a) the acid chloride (II) is initially charged,
b) a pressure of from 0 to 700 mbar is established,
c) the arylamine (III) is metered in an approximately stoichiometric amount and
d) the product of value is isolated.

10 Claims, No Drawings

OTHER PUBLICATIONS

Kundu, N. G., et al., "Palladium-Catalysed Heteroannulation with Terminal Alkynes: a Highly Regio- and Stereoselective Synthesis of (Z)-3-Aryl(alkyl)idene Isoindolin-1-ones", *Tetrahedron*, (2000) 56, 4777-4792.

Ott, E., "Uber die Konstitution und das Tautomerie-Gleichgewicht der beiden Phthalsaure-tetrachloride", *Chemische Berichte*, (1922) 55, 2108-2125.

Khan, M.W., et al., "Palladium mediated synthesis of isoindolinones and isoquinolinones", *Tetrahedron*, (2005) 61, 11204-11210.

Kundu, N.G., et al., "Palladium-Catalysed Heteroannulation with Terminal Alkynes: a Highly Regio- and Stereoselective Synthesis of (Z)-3-Aryl(alkyl)idene Isoindolin-1-ones", *Tetrahedron*, (2000) 56, 4777-4792.

Larock, R.C., "7. From Nitro Compounds", *Comprehensive Organic Transformations*. A Guide to Functional Group Preparations (Second Edition), Wiley-VCH, pp. 821-829, 1999.

Larock, R.C., "9. Interconversion of Nitriles, Carboxylic Acids and Derivatives" *Comprehensive Organic Transformations*. A Guide to Functional Group Preparations (Second Edition), Wiley-VCH, pp. 1929-1930, 1999.

Ott, E., "Uber die Konstitution and das Tautomerie-Gleichgewicht der beiden Phthalsaure-tetrachloride", *Chemische Berichte*, (1922) 55, 2108-2125.

Yildirim, I., et al., "Experimental and theoretical studies on the functionalization reactions of 4-benzoyl-1,5-diphenyl-1H-pyriazole-3-carboxylic acid and acid chloride with various aminophenols", *Struct. Chem.*, (2006) 17, 241-247.

METHOD FOR MANUFACTURING ARYL CARBOXAMIDES

This application is a National Stage application of International Application No. PCT/EP2009/055446 filed May 6, 2009, the entire contents of which is hereby incorporated herein by reference. This application also claims priority under 35 U.S.C. §119 to European Patent Application No. 08155888.4, filed May 8, 2008, the entire contents of which is hereby incorporated herein by reference.

The present invention relates to a process for preparing arylcarboxamides of the formula (I)

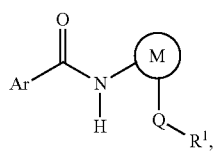

(I)

where the substituents are each defined as follows:

Ar is a mono- to trisubstituted phenyl, pyridyl or pyrazolyl ring, where the substituents are each independently selected from halogen, $C_1$-$C_4$-alkyl and $C_1$-$C_4$-haloalkyl;

M is thienyl or phenyl, which may bear a halogen substituent;

Q is a direct bond, cyclopropylene, a fused bicyclo[2.2.1] heptane or bicyclo[2.2.1]heptene ring;

$R^1$ is hydrogen, halogen, $C_1$-$C_6$-alkyl, $C_1$-$C_4$-alkoxy, $C_1$-$C_4$-haloalkoxy, mono- to trisubstituted phenyl, where the substituents are each independently selected from halogen and trifluoromethylthio, or cyclopropyl;

by reacting an acid chloride of the formula (II)

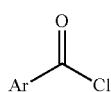

(II)

with an arylamine (III)

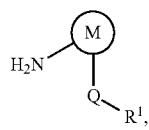

(III)

in a suitable nonaqueous solvent.

JP-A 2001/172276 discloses that alkyl- or phenylcarbonyl chlorides can be reacted with arylamines under reduced pressure. The reactions described are carried out without an auxiliary base, but in highly dilute solutions. For an industrial scale preparation of the arylcarboxamides (I), this process is, however, unsuitable owing to the large amounts of solvent. A more concentrated mode of operation is not possible, since this leads to lump formation and mixing problems, which greatly reduces the yield of product of value.

Other processes described in the literature for preparing carboxamides from acid chloride and arylamine without use of an auxiliary base (cf., for example, Journal of Combinatorial Chemistry (2003), 5(3), 253-259, Structural Chemistry (2006), 17(2), 241-247 and JP-A 1973/049217) are not usable on the industrial scale, because they afford the desired products of value only in poor yields.

It was accordingly an object of the present invention to provide a process usable on the industrial scale for preparing the arylcarboxamides (I).

Accordingly, it has been found that the arylcarboxamides (I) are obtainable in high yields by, in the absence of an auxiliary base, a) initially charging the acid chloride (II),
b) establishing a pressure of from 0 to 700 mbar,
c) metering in the arylamine (III) in an approximately stoichiometric amount and
d) isolating the product of value.

The acid chlorides (II) are either commercially available or can be prepared, for example, according to R. C. Larock, Comprehensive Organic Transformations, Verlage Wiley-VCH, 2nd Edition 1999, pages 1929 ff.

The arylamines (III) are generally obtainable by hydrogenating the corresponding nitroaromatics. Further details can be found, for example, in R. C. Larock, Comprehensive Organic Transformations, Verlage Wiley-VCH, 2nd Edition 1999, pages 821 ff.

The term "halogen" in each case denotes fluorine, chlorine, bromine or iodine, preferably fluorine or chlorine;

"$C_1$-$C_6$-alkyl", as used herein, denotes a saturated straight-chain or branched hydrocarbon group comprising from 1 to 6 carbon atoms, especially from 1 to 4 carbon atoms, for example methyl, ethyl, propyl, 1-methylethyl, butyl, 1-methylpropyl, 2-methylpropyl, 1,1-dimethylethyl, pentyl, 1-methylbutyl, 2-methylbutyl, 3-methylbutyl, 2,2-dimethylpropyl, 1-ethylpropyl, hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl, 1-ethyl-2-methylpropyl and isomers thereof. $C_1$-$C_4$-Alkyl comprises, for example, methyl, ethyl, propyl, 1-methylethyl, butyl, 1-methylpropyl, 2-methylpropyl or 1,1-dimethylethyl.

"$C_1$-$C_4$-haloalkyl" represents a partly or fully halogenated $C_1$-$C_4$-alkyl radical, where the halogen atom(s) is/are especially fluorine, chlorine and/or bromine, i.e., for example, chloromethyl, bromomethyl, dichloromethyl, trichloromethyl, fluoromethyl, difluoro-methyl, trifluoromethyl, chlorofluoromethyl, dichlorofluoromethyl, chlorodifluoromethyl, 1-chloroethyl, 1-bromoethyl, 1-fluoroethyl, 2-fluoroethyl, 2,2-difluoroethyl, 2-chloro-2-fluoroethyl, 2,2,2-trifluoroethyl, 2-chloro-1,1,2-trifluoroethyl, 2-chloro-2,2-difluoroethyl, 2-bromo-2,2-difluoroethyl, 2,2-dichloro-2-fluoroethyl, 2,2,2-trichloroethyl, 1,1,2,2-tetrafluoroethyl, 1,1,2,2-tetrachloroethyl, pentafluoroethyl, 2,2,3,3-tetrafluoro-1-propyl, 1,1,2,3,3,3-hexafluoro-1-propyl, 1,1,1,3,3,3-hexafluoro-2-propyl, heptafluoro-1-propyl, heptafluoro-2-propyl, 2,2,3,3,4,4,4-heptafluoro-1-butyl or nonafluoro-1-butyl, especially halomethyl, more preferably $CH(F)_2$ and $CF_3$;

"$C_1$-$C_4$-alkoxy" represents methoxy, ethoxy, n-propoxy, 1-methylethoxy, n-butoxy, 1-methylpropoxy, 2-methylpropoxy or 1,1-dimethylethoxy, especially 1-methylethoxy;

"$C_1$-$C_4$-haloalkoxy" represents a partly or fully halogenated $C_1$-$C_4$-alkoxy radical, where the halogen atom(s) is/are especially fluorine, chlorine and/or bromine, i.e., for example, $OCH_2Cl$, $OCH_2Br$, $OCHCl_2$, $OC(Cl)_3$, $OCH_2F$, $OCHF_2$, $OCF_3$, $OCHFCl$, $OCFCl_2$, $OCF_2Cl$, $OCHCl$—$CH_3$, $OCHBr$—$CH_3$, $OCHF$—$CH_3$, $OCH_2$—$CH_2F$, $OCH_2$—$CHF_2$, $OCH_2$—$CHFCl$, $OCH_2$—$CF_3$, $OCF_2$—$CHFCl$, OCH$_2$—CF$_2$Cl, OCH$_2$—CF$_2$Br, OCH$_2$—CFCl$_2$, OCH$_2$—C(Cl)$_3$, OCF$_2$—CHF$_2$, OC(Cl)$_2$—CHCl$_2$, OC$_2$F$_5$, OCH$_2$—CF$_2$—CHF$_2$, OCF$_2$—CHF—CF$_3$, OCH(CF$_3$)$_2$, O(n-C$_3$F$_7$), OCF(CF$_3$)$_2$, 2,2,3,3,4,4,4-heptafluoro-1-butoxy or nonafluoro-1-butoxy, especially OCF$_2$—CHF—CF$_3$.

The preparation of the following arylcarboxamides (I) is preferred:

benodanil, bixafen, boscalid, flutolanil, mepronil, penthiopyrad, N-(2-bicyclopropyl-2-ylphenyl)-3-difluoromethyl-1-methylpyrazol-4-ylcarboxamide, N-(3',4',5'-trifluorobiphenyl-2-yl)-1,3-dimethylpyrazol-4-ylcarboxamide, N-(3',4',5'-trifluorobiphenyl-2-yl)-1,3-dimethyl-5-fluoropyrazol-4-ylcarboxamide, N-(3',4',5'-trifluorobiphenyl-2-yl)-5-chloro-1,3-dimethylpyrazol-4-ylcarboxamide, N-(3',4',5'-trifluorobiphenyl-2-yl)-3-fluoromethyl-1-methylpyrazol-4-ylcarboxamide, N-(3',4',5'-trifluorobiphenyl-2-yl)-3-(chlorofluoromethyl)-1-methylpyrazol-4-ylcarboxamide, N-(3',4',5'-trifluorobiphenyl-2-yl)-3-difluoromethyl-1-methylpyrazol-4-ylcarboxamide, N-(3',4',5'-trifluorobiphenyl-2-yl)-3-difluoromethyl-5-fluoro-1-methylpyrazol-4-ylcarboxamide, N-(3',4',5'-trifluorobiphenyl-2-yl)-5-chloro-3-difluoromethyl-1-methylpyrazol-4-ylcarboxamide, N-(3',4',5'-trifluorobiphenyl-2-yl)-3-(chlorodifluoromethyl)-1-methylpyrazol-4-ylcarboxamide, N-(3',4',5'-trifluorobiphenyl-2-yl)-1-methyl-3-trifluoromethylpyrazol-4-ylcarboxamide, N-(3',4',5'-trifluorobiphenyl-2-yl)-5-fluoro-1-methyl-3-trifluoromethylpyrazol-4-ylcarboxamide, N-(3',4',5'-trifluorobiphenyl-2-yl)-5-chloro-1-methyl-3-trifluoromethylpyrazol-4-ylcarboxamide, N-(2',4',5'-trifluorobiphenyl-2-yl)-1,3-dimethylpyrazol-4-ylcarboxamide, N-(2',4',5'-trifluorobiphenyl-2-yl)-1,3-dimethyl-5-fluoropyrazol-4-ylcarboxamide, N-(2',4',5'-trifluorobiphenyl-2-yl)-5-chloro-1,3-dimethylpyrazol-4-ylcarboxamide, N-(2',4',5'-trifluorobiphenyl-2-yl)-3-fluoromethyl-1-methylpyrazol-4-ylcarboxamide, N-(2',4',5'-trifluorobiphenyl-2-yl)-3-(chlorofluoromethyl)-1-methylpyrazol-4-ylcarboxamide, N-(2',4',5'-trifluorobiphenyl-2-yl)-3-difluoromethyl-1-methylpyrazol-4-ylcarboxamide, N-(2',4',5'-trifluorobiphenyl-2-yl)-3-difluoromethyl-5-fluoro-1-methylpyrazol-4-ylcarboxamide, N-(2',4',5'-trifluorobiphenyl-2-yl)-5-chloro-3-difluoromethyl-1-methylpyrazol-4-ylcarboxamide, N-(2',4',5'-trifluorobiphenyl-2-yl)-3-(chlorodifluoromethyl)-1-methylpyrazol-4-ylcarboxamide, N-(2',4',5'-trifluorobiphenyl-2-yl)-1-methyl-3-trifluoromethylpyrazol-4-ylcarboxamide, N-(2',4',5'-trifluorobiphenyl-2-yl)-5-fluoro-1-methyl-3-trifluoromethylpyrazol-4-ylcarboxamide, N-(2',4',5'-trifluorobiphenyl-2-yl)-5-chloro-1-methyl-3-trifluoromethylpyrazol-4-ylcarboxamide, N-(3',4'-dichloro-3-fluorobiphenyl-2-yl)-1-methyl-3-trifluoromethyl-1H-pyrazol-4-ylcarboxamide, N-(3',4'-dichloro-3-fluorobiphenyl-2-yl)-1-methyl-3-difluoromethyl-1H-pyrazol-4-ylcarboxamide, N-(3',4'-difluoro-3-fluorobiphenyl-2-yl)-1-methyl-3-trifluoromethyl-1H-pyrazol-4-carboxamide, N-(3',4'-difluoro-3-fluorobiphenyl-2-yl)-1-methyl-3-difluoromethyl-1H-pyrazol-4-ylcarboxamide, N-(3'-chloro-4'-fluoro-3-fluorobiphenyl-2-yl)-1-methyl-3-difluoromethyl-1H-pyrazol-4-ylcarboxamide, N-(3',4'-dichloro-4-fluorobiphenyl-2-yl)-1-methyl-3-trifluoromethyl-1H-pyrazol-4-ylcarboxamide, N-(3',4'-difluoro-4-fluorobiphenyl-2-yl)-1-methyl-3-trifluoromethyl-1H-pyrazol-4-ylcarboxamide, N-(3',4'-dichloro-4-fluorobiphenyl-2-yl)-1-methyl-3-difluoromethyl-1H-pyrazol-4-ylcarboxamide, N-(3',4'-difluoro-4-fluorobiphenyl-2-yl)-1-methyl-3-difluoromethyl-1H-pyrazol-4-ylcarboxamide, N-(3'-chloro-4'-fluoro-4-fluorobiphenyl-2-yl)-1-methyl-3-difluoromethyl-1H-pyrazol-4-ylcarboxamide, N-(3',4'-dichloro-5-fluorobiphenyl-2-yl)-1-methyl-3-trifluoromethyl-1H-pyrazol-4-ylcarboxamide, N-(3',4'-difluoro-5-fluorobiphenyl-2-yl)-1-methyl-3-trifluoromethyl-1H-pyrazol-4-ylcarboxamide, N-(3',4'-dichloro-5-fluorobiphenyl-2-yl)-1-methyl-3-difluoromethyl-1H-pyrazol-4-ylcarboxamide, N-(3',4'-difluoro-5-fluorobiphenyl-2-yl)-1-methyl-3-difluoromethyl-1H-pyrazol-4-ylcarboxamide, N-(3',4'-dichloro-5-fluorobiphenyl-2-yl)-1,3-dimethyl-1H-pyrazol-4-ylcarboxamide, N-(3'-chloro-4'-fluoro-5-fluorobiphenyl-2-yl)-1-methyl-3-difluoromethyl-1H-pyrazol-4-ylcarboxamide, N-(4'-fluoro-4-fluorobiphenyl-2-yl)-1-methyl-3-trifluoromethyl-1H-pyrazol-4-ylcarboxamide, N-(4'-fluoro-5-fluorobiphenyl-2-yl)-1-methyl-3-trifluoromethyl-1H-pyrazol-4-ylcarboxamide, N-(4'-chloro-5-fluorobiphenyl-2-yl)-1-methyl-3-trifluoromethyl-1H-pyrazol-4-ylcarboxamide, N-(4'-methyl-5-fluorobiphenyl-2-yl)-1-methyl-3-trifluoromethyl-1H-pyrazol-4-ylcarboxamide, N-(4'-fluoro-5-fluorobiphenyl-2-yl)-1,3-dimethyl-1H-pyrazol-4-ylcarboxamide, N-(4'-chloro-5-fluorobiphenyl-2-yl)-1,3-dimethyl-1H-pyrazol-4-ylcarboxamide, N-(4'-methyl-5-fluorobiphenyl-2-yl)-1,3-dimethyl-1H-pyrazol-4-ylcarboxamide, N-(4'-fluoro-6-fluorobiphenyl-2-yl)-1-methyl-3-trifluoromethyl-1H-pyrazol-4-ylcarboxamide, N-[2-(1,1,2,3,3,3-hexafluoropropoxy)phenyl]-3-difluoromethyl-1-methyl-1H-pyrazol-4-ylcarboxamide, N-[4'-(trifluoromethylthio)biphenyl-2-yl]-3-difluoromethyl-1-methyl-1H-pyrazol-4-ylcarboxamide, N-[4'-(trifluoromethylthio)biphenyl-2-yl]-1-methyl-3-trifluoromethyl-1-methyl-1H-pyrazol-4-ylcarboxamide, 3-(difluoromethyl)-1-methyl-N[1,2,3,4-tetrahydro-9-(1-methylethyl)-1,4-methanonaphthalen-5-yl]-1H-pyrazol-4-ylcarboxamide, N-(3'-chloro-5-fluorobiphenyl-2-yl)-3-(difluoromethyl)-1-methylpyrazol-4-ylcarboxamide, N-(4'-chloro-5-fluorobiphenyl-2-yl)-3-(difluoromethyl)-1-methylpyrazol-4-ylcarboxamide, N-(4'-chlorobiphenyl-2-yl)-3-(difluoromethyl)-1-methylpyrazol-4-ylcarboxamide, N-(4'-bromobiphenyl-2-yl)-3-(difluoromethyl)-1-methylpyrazol-4-ylcarboxamide, N-(4'-iodobiphenyl-2-yl)-3-(difluoromethyl)-1-methylpyrazol-4-ylcarboxamide, N-(3',5'-difluorobiphenyl-2-yl)-3-(difluoromethyl)-1-methylpyrazol-4-ylcarboxamide, N-(2-chloro-4-fluorophenyl)-3-(difluoromethyl)-1-methylpyrazol-4-ylcarboxamide, N-(2-bromo-4-fluorophenyl)-3-(difluoromethyl)-1-methylpyrazol-4-ylcarboxamide, N-(2-iodo-4-fluorophenyl)-3-(difluoromethyl)-1-methylpyrazol-4-ylcarboxamide or N-[2-(1,3-dimethylbutyl)phenyl]-1,3-dimethyl-5-fluoro-1H-pyrazol-4-ylcarboxamide.

Particular preference is given to those carboxamides (I) in which

Ar is a mono- to trisubstituted pyridyl or pyrazolyl ring, where the substituents are each independently selected from halogen, $C_1$-$C_4$-alkyl and $C_1$-$C_4$-haloalkyl. Very particular preference is given to those carboxamides (I) in which Ar is a di- or trisubstituted pyrazolyl ring, where the substituents are each independently selected from halogen, $C_1$-$C_4$-alkyl and $C_1$-$C_4$-haloalkyl, especially fluorine, chlorine, methyl, difluoromethyl and trifluoromethyl.

According to the invention, the reaction is conducted without an auxiliary base in an organic solvent which is substantially anhydrous. A low water content is understood to mean from about 0.5 g to 5 g of water per mole of acid chloride (II) used. Larger amounts of water should be avoided, since the water would lead to an increased consumption of feedstocks.

Usable solvents are, for example, aromatic hydrocarbons such as toluene, o-, m-, p-xylene, mesitylene, ethylbenzene and chlorobenzene, halogenated aliphatic hydrocarbons such as tetrachloroethane and dichloroethylene, ethers such as methyl tert-butyl ethyl, tetrahydrofuran and dioxane or mixtures of the solvents mentioned. Particularly preferred solvents are the aromatic hydrocarbons, especially toluene and o-, m-, p-xylene.

According to the invention, the acid chloride (II) is initially charged, the desired pressure is established and the arylamine (III) is metered in. Metered addition is understood to mean both the addition of (III) in portions and the continuous addition of (III)

a) to the surface of the solution of (II) or
b) directly into the solution of (II), as an "immersed mode of reaction".

The pressure is generally selected such that the reaction mixture boils.

It is normal to work at a pressure between 0 and 700 mbar and a reaction temperature of from 20 to 120° C., preferably at from 200 to 600 mbar and from 70 to 100° C., especially at from 350 to 450 mbar and 80 to 90° C.

Acid chloride (II) and arylamine (III) are used in about equimolar amounts, or one of the components is used in a slight excess of up to 10 mol %. The molar ratio of (III) to (II) is thus generally from 0.9:1 to 1.1:1, preferably from about 1.0 to 1.1.

The metered addition of (III), preferably dissolved in the organic solvent in which (II) has also been initially charged, is effected typically over the course of from 0.5 to 20 hours, especially from 2 to 10 hours, more preferably from 3 to 5 hours.

The carboxamide (I) is released from the reaction mixture preferably by direct crystallization or by treatment of the reaction mixture with a suitable base and subsequent crystallization, for example at from (−20) to 20° C.

Suitable bases for this purpose are alkali metal hydroxides such as sodium and potassium hydroxide, alkali metal carbonates such as sodium and potassium carbonate, alkali metal hydrogencarbonates such as sodium and potassium hydrogencarbonate, alkali metal phosphates such as sodium and potassium phosphate, alkali metal hydrogenphosphates such as sodium and potassium hydrogen-phosphate, alkali metal dihydrogenphosphates such as sodium and potassium dihydrogenphosphate, and also nitrogen bases such as ammonia. Particular preference is given to the alkali metal hydroxides such as sodium and potassium hydroxide, alkali metal carbonates such as sodium and potassium carbonate, and also to the alkali metal hydrogencarbonates such as sodium and potassium hydrogencarbonate.

The base can be used in solid form or in the form of its commercial aqueous solutions. Preference is given to using a from 1 to 20% by weight aqueous solution, the amount preferably being such that the pH of the solution is from 3 to 12, preferably from 7 to 10.

The crystalline product of value can finally be removed by means of customary methods, for example filtration.

The process products (I) are valuable active ingredients in crop protection.

WORKING EXAMPLES

Example 1

Synthesis of N-(3',4',5'-trifluorobiphenyl-2-yl)-3-difluoromethyl-1-methyl-1H-pyrazole-4-carboxamide 100.0 g (0.504 mol, 98% pure) of 3-difluoromethyl-1-methyl-1H-pyrazole-4-carbonyl chloride were dissolved at 25° C. in 257.2 g of toluene. The solution was evacuated to 400 mbar and heated to 85° C. Subsequently, within 3 hours, 492.8 g (0.499 mol, 23% strength) of toluenic 3',4',5'-trifluorobiphenyl-2-ylamine solution were metered in, after which stirring was continued for another 1 hour. After venting and cooling to 25° C. with a ramp of 10° C./h, the mixture was stirred overnight. Subsequently, the mixture was cooled to 0° C., and the solid constituents were filtered off, washed with cold toluene and dried at 80° C. under reduced pressure. The yield (without further processing of the mother liquor) was 177.7 g (92%).

Example 1a

Comparative Test

Synthesis of N-(3',4',5'-trifluorobiphenyl-2-yl)-3-difluoromethyl-1-methyl-1H-pyrazole-4-carboxamide Analogous Mode of Reaction to Example 1 from JP-A 2001/172276, p. 10

19.0 g (0.085 mol, 99.8% pure) of 3',4',5'-trifluorobiphenyl-2-ylamine were dissolved in 400.0 g of toluene. Within 1 min, 17.7 g (0.089 mol, 98.1% pure) of 3-difluoromethyl-1-methyl-1H-pyrazole-4-carbonyl chloride were added at 25° C. Subsequently, the reaction mixture was evacuated to 72 mbar and heated to 40° C. for 3 hours. After 15 min, a white solid formed, which was later converted to a viscous, gel-like suspension. After cooling to 0° C., the mixture was filtered through a glass frit (very slow, blockages) and the filtercake was washed with cold toluene. The residue was dried under reduced pressure and afforded 15.0 g of a mixture of 3',4',5'-trifluorobiphenyl-2-ylamine hydrochloride (40% by weight) and N-(3',4',5'-trifluorobiphenyl-2-yl)-3-difluoromethyl-1-methyl-1H-pyrazole-4-carboxamide (48% by weight). The mother liquor (375.0 g) comprised 2.8% by weight of N-(3',4',5'-trifluorobiphenyl-2-yl)-3-difluoromethyl-1-methyl-1H-pyrazole-4-carboxamide. Purely theoretically, the yield was thus approx. 54%.

Example 2

Synthesis of N-(3',5'-difluorobiphenyl-2-yl)-3-difluoromethyl-1-methyl-1H-pyrazole-4-carboxamide 38.9 g (0.196 mol, 98% pure) of 3-difluoromethyl-1-methyl-1H-pyrazole-4-carbonyl chloride were dissolved at 25° C. in 100.0 g of toluene. The solution was evacuated to 400 mbar and heated to 85° C. Subsequently, within 1.5 hours, 173.0 g (0.194 mol, 23% strength) of toluenic 3',4'-difluorobiphenyl-2-ylamine solution were metered in and the reaction mixture was stirred for a further 1 hour. After venting and cooling to room temperature, the mixture was concentrated to volume approx. 100 ml under reduced pressure. The solids were filtered off, washed with n-hexane and dried at 85° C.

under reduced pressure. The yield (without further processing of the mother liquor) was 46.5 g (66%).

Example 3

Synthesis of N-(3',4',5'-trifluorobiphenyl-2-yl)-1,3-dimethyl-1H-pyrazole-4-carboxamide 79.1 g (0.494 mol, 99% pure) of 1,3-dimethyl-1H-pyrazole-4-carbonyl chloride were dissolved at 25° C. in 257.2 g of toluene. The solution was evacuated to 400 mbar and heated to 85° C. Subsequently, within 3 hours, 483.0 g (0.489 mol, 23% strength) of toluenic 3',4',5'-trifluorobiphenyl-2-ylamine solution were metered in and the reaction mixture was stirred for a further 1 hour. After venting and cooling to 70° C., the mixture was cooled to 20° C. with a cooling ramp of 5° C./h and stirred overnight. Subsequently, the mixture was cooled to 0° C., and the solids were filtered off, washed with cold toluene and dried at 80° C. under reduced pressure. The yield (without further processing of the mother liquor) was 155.4 g (92%).

Example 4

Synthesis of N-(2-chlorophenyl)-3-difluoromethyl-1-methyl-1H-pyrazole-4-carboxamide 80.0 g (0.403 mol, 98% pure) of 3-difluoromethyl-1-methyl-1H-pyrazole-4-carbonyl chloride were dissolved at 25° C. in 257.2 g of toluene. The solution was evacuated to 400 mbar and heated to 85° C. Subsequently, within 3 hours, 221.3 g (0.399 mol, 23% strength) of toluenic 2-chloroaniline solution were metered in and the reaction mixture was stirred for a further 1 hour. After venting and cooling to 20° C. with a ramp of 10° C./h, the mixture was stirred overnight. Subsequently, the mixture was cooled to 0° C., and the solids were filtered off, washed with cold toluene and dried at 80° C. under reduced pressure. The yield (without further processing of the mother liquor) was 105 g (92%).

Example 5

Synthesis of N-(3',4'-dichloro-5-fluorobiphenyl-2-yl)-3-difluoromethyl-1-methyl-1H-pyrazole-4-carboxamide 5.6 g (0.029 mol, 98% pure) of 3-difluoromethyl-1-methyl-1H-pyrazole-4-carbonyl chloride were dissolved at 25° C. in 10.4 g of toluene. The solution was evacuated to 400 mbar and heated to 85° C. Subsequently, within 5 minutes, 7.8 g (0.030 mol, approx. 92% pure) of 3',4'-dichloro-5-fluorobiphenyl-2-ylamine, dissolved in 28 g of toluene, were metered in and the reaction mixture was stirred for a further 1 hour. After venting and cooling to 25° C. overnight, the mixture was cooled further to 0° C., and the solids were filtered off, washed with cold toluene and dried at 80° C. under reduced pressure. The yield (without further processing of the mother liquor) was 8.1 g (71%).

Example 6

Synthesis of N-(2-bicyclopropyl-2-ylphenyl)-3-difluoromethyl-1-methyl-1H-pyrazole-4-carboxamide 16.7 g (0.086 mol, 98% pure) of 3-difluoromethyl-1-methyl-1H-pyrazole-4-carbonyl chloride were dissolved at 25° C. in 48.0 g of toluene. The solution was evacuated to 400 mbar and heated to 85° C. Subsequently, within 45 min, 15.0 g (0.087 mol) of 2-bicyclopropyl-2-ylphenylamine, dissolved in 51.6 g of toluene, were metered in and the reaction mixture was stirred for another 1 h. After venting and cooling to 25° C., the mixture was stirred overnight. Subsequently, the mixture was concentrated under reduced pressure and dried. The yield was 27.3 g (96%).

Example 7

Synthesis of N-(9-isopropyl-1,2,3,4-tetrahydro-1,4-methanonaphthalen-5-yl)-3-difluoromethyl-1-methyl-1H-pyrazole-4-carboxamide 15.1 g (0.0752 mol, 96.5% pure) of 3-difluoromethyl-1-methyl-1H-pyrazole-4-carbonyl chloride were dissolved at 25° C. in 100 ml of toluene. The solution was evacuated to 350 mbar and heated to 85° C. Subsequently, within 60 min, 20 g (0.074 mol, 75%; 65:10 syn/anti isomer mixture) of 9-isopropyl-1,2,3,4-tetrahydro-1,4-methanonaphthalen-5-ylamine, dissolved in 100 ml of toluene, were metered in and the reaction mixture was stirred for another 1 hour. After venting and cooling to 25° C., the mixture was stirred overnight. Subsequently, the mixture was concentrated under reduced pressure and dried. The yield was 31.3 g; according to 1H NMR 70% pure (82%).

Example 8

Synthesis of 2-chloro-N-(4'-chlorobiphenyl-2-yl) nicotinamide 100.0 g (0.557 mol, 98% pure) of 3-difluoromethyl-1-methyl-1H-pyrazole-4-carbonyl chloride were dissolved at 25° C. in 80.0 g of toluene. The solution was evacuated to 200 mbar and heated to 95° C. Subsequently, within 2.5 hours, 396.8 g (0.541 mol, 28% strength) of xylenic 4'-chlorobiphenyl-2-ylamine solution were metered in and the reaction mixture was stirred for a further 1 hour. After venting and cooling to 87° C., the mixture was seeded with 1 g of 2-chloro-N-(4'-chlorobiphenyl-2-yl)nicotinamide and the temperature was maintained for 1 hour. Subsequently, the mixture was cooled to 25° C. with a ramp of 5° C./h. After further cooling to 10-15° C., the solids were filtered off, washed with cold xylene and dried at 80° C. under reduced pressure. The yield (without further processing of the mother liquor) was 166.4 g (73%). HPLC shows the desired product and the diacylated product in a ratio of 85:15 area %.

The invention claimed is:
1. A process for preparing a compound of the formula (I)

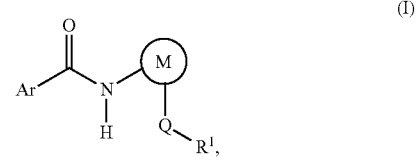

wherein
Ar is a mono- to trisubstituted phenyl, pyridyl or pyrazolyl ring, where the substituents are each independently selected from the group consisting of halogen, $C_1$-$C_4$-alkyl and $C_1$-$C_4$-haloalkyl;
M is thienyl or phenyl, which may bear a halogen substituent;

Q is a direct bond, cyclopropylene, a fused bicyclo[2.2.1]heptane or bicyclo[2.2.1]heptene ring;

$R^1$ is hydrogen, halogen, $C_1$-$C_6$-alkyl, $C_1$-$C_4$-alkoxy, $C_1$-$C_4$-haloalkoxy, mono- to trisubstituted phenyl, wherein the substituents are each independently selected from the group consisting of halogen and trifluoromethylthio, or cyclopropyl;

by reacting an acid chloride of the formula (II)

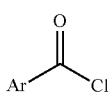
(II)

with an arylamine (III)

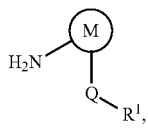
(III)

in a suitable nonaqueous solvent,
which comprises, in the absence of an auxiliary base,
a) initially charging the acid chloride (II),
b) establishing a pressure of from 0 to 700 mbar,
c) metering in the arylamine (III) in an approximately stoichiometric amount and
d) isolating the compound of formula (I).

2. The process according to claim 1, wherein Ar is a phenyl, pyridyl or pyrazolyl ring

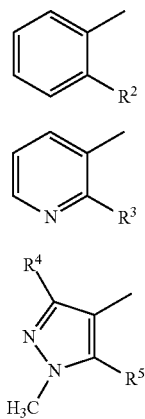

wherein
$R^2$ is halogen, methyl or trifluoromethyl;
$R^3$ is halogen;
$R^4$ is $C_1$-$C_4$-alkyl or $C_1$-$C_4$-haloalkyl and
$R^5$ is hydrogen or halogen.

3. The process according to claim 1, wherein M is phenyl, Q is cyclopropylene and $R^1$ is cyclopropyl.

4. The process according to claim 1, wherein M is phenyl, Q is a bond and $R^1$ is isopropoxy or mono- to trisubstituted phenyl, where the substituents are each independently selected from the group consisting of halogen and trifluoromethylthio.

5. The process according to claim 1, wherein M is phenyl substituted by one halogen, Q is a bond and $R^1$ is hydrogen or mono- to tri-halogen-substituted phenyl.

6. The process according to claim 1, wherein the compound of formula (I) is benodanil, bixafen, boscalid, flutolanil, mepronil, penthiopyrad, N-(2-bicyclopropyl-2-ylphenyl)-3-difluoromethyl-1-methylpyrazol-4-ylcarboxamide, N-(3',4',5'-trifluorobiphenyl-2-yl)-1,3-dimethylpyrazol-4-ylcarboxamide, N-(3',4',5'-trifluorobiphenyl-2-yl)-1,3-dimethyl-5-fluoropyrazol-4-ylcarboxamide, N-(3',4',5'-trifluorobiphenyl-2-yl)-5-chloro-1,3-dimethylpyrazol-4-ylcarboxamide, N-(3',4',5'-trifluorobiphenyl-2-yl)-3-fluoromethyl-1-methylpyrazol-4-ylcarboxamide, N-(3',4',5'-trifluorobiphenyl-2-yl)-3-(chlorofluoromethyl)-1-methylpyrazol-4-ylcarboxamide, N-(3',4',5'-trifluorobiphenyl-2-yl)-3-difluoromethyl-1-methylpyrazol-4-ylcarboxamide, N-(3',4',5'-trifluorobiphenyl-2-yl)-3-difluoromethyl-5-fluoro-1-methylpyrazol-4-ylcarboxamide, N-(3',4',5'-trifluorobiphenyl-2-yl)-5-chloro-3-difluoromethyl-1-methylpyrazol-4-ylcarboxamide, N-(3',4',5'-trifluorobiphenyl-2-yl)-3-(chlorodifluoromethyl)-1-methylpyrazol-4-ylcarboxamide, N-(3',4',5'-trifluorobiphenyl-2-yl)-1-methyl-3-trifluoromethylpyrazol-4-ylcarboxamide, N-(3',4',5'-trifluorobiphenyl-2-yl)-5-fluoro-1-methyl-3-trifluoromethylpyrazol-4-ylcarboxamide, N-(3',4',5'-trifluorobiphenyl-2-yl)-5-chloro-1-methyl-3-trifluoromethylpyrazol-4-ylcarboxamide, N-(2',4',5'-trifluorobiphenyl-2-yl)-1,3-dimethylpyrazol-4-ylcarboxamide, N-(2',4',5'-trifluorobiphenyl-2-yl)-1,3-dimethyl-5-fluoropyrazol-4-ylcarboxamide, N-(2',4',5'-trifluorobiphenyl-2-yl)-5-chloro-1,3-dimethylpyrazol-4-ylcarboxamide, N-(2',4',5'-trifluorobiphenyl-2-yl)-3-fluoromethyl-1-methylpyrazol-4-ylcarboxamide, N-(2',4',5'-trifluorobiphenyl-2-yl)-3-(chlorofluoromethyl)-1-methylpyrazol-4-ylcarboxamide, N-(2',4',5'-trifluorobiphenyl-2-yl)-3-difluoromethyl-1-methylpyrazol-4-ylcarboxamide, N-(2',4',5'-trifluorobiphenyl-2-yl)-3-difluoromethyl-5-fluoro-1-methylpyrazol-4-ylcarboxamide, N-(2',4',5'-trifluorobiphenyl-2-yl)-5-chloro-3-difluoromethyl-1-methylpyrazol-4-ylcarboxamide, N-(2',4',5'-trifluorobiphenyl-2-yl)-3-(chlorodifluoromethyl)-1-methylpyrazol-4-ylcarboxamide, N-(2',4',5'-trifluorobiphenyl-2-yl)-1-methyl-3-trifluoromethylpyrazol-4-ylcarboxamide, N-(2',4',5'-trifluorobiphenyl-2-yl)-5-fluoro-1-methyl-3-trifluoromethylpyrazol-4-ylcarboxamide, N-(2',4',5'-trifluorobiphenyl-2-yl)-5-chloro-1-methyl-3-trifluoromethylpyrazol-4-ylcarboxamide, N-(3',4'-dichloro-3-fluorobiphenyl-2-yl)-1-methyl-3-trifluoromethyl-1H-pyrazol-4-ylcarboxamide, N-(3',4'-dichloro-3-fluorobiphenyl-2-yl)-1-methyl-3-difluoromethyl-1H-pyrazol-4-ylcarboxamide, N-(3',4'-difluoro-3-fluorobiphenyl-2-yl)-1-methyl-3-trifluoromethyl-1H-pyrazol-4-carboxamide, N-(3',4'-difluoro-3-fluorobiphenyl-2-yl)-1-methyl-3-difluoromethyl-1H-pyrazol-4-ylcarboxamide, N-(3'-chloro-4'-fluoro-3-fluorobiphenyl-2-yl)-1-methyl-3-difluoromethyl-1H-pyrazol-4-ylcarboxamide, N-(3',4'-dichloro-4-fluorobiphenyl-2-yl)-1-methyl-3-trifluoromethyl-1H-pyrazol-4-ylcarboxamide, N-(3',4'-difluoro-4-fluorobiphenyl-2-yl)-1-methyl-3-trifluoromethyl-1H-pyrazol-4-ylcarboxamide, N-(3',4'-dichloro-4-fluorobiphenyl-2-yl)-1-methyl-3-difluoromethyl-1H-pyrazol-4-ylcarboxamide, N-(3',4'-difluoro-4-fluorobiphenyl-2-yl)-1-methyl-3-difluoromethyl-1H-pyrazol-4-ylcarboxamide, N-(3'-chloro-4'-fluoro-4-fluorobiphenyl-2-yl)-1-methyl-3-difluoromethyl-1H-pyrazol-4-ylcarboxamide, N-(3',4'-dichloro-5-fluorobiphenyl-2-yl)-1-methyl-3-trifluoromethyl-1H-pyrazol-4-ylcarboxamide, N-(3',4'-difluoro-5-fluorobiphenyl-2-yl)-1-methyl-3-trifluoromethyl-1H-pyrazol-4-ylcarboxamide, N-(3',4'-dichloro-5-fluorobiphenyl-2-yl)-1-methyl-3-difluoromethyl-1H-pyrazol-4-ylcarboxamide, N-(3',4'-difluoro-5-fluorobiphenyl-2-yl)-1-methyl-3-difluoromethyl-1H-pyrazol-4-ylcarboxamide, N-(3',4'-dichloro-5-fluorobiphenyl-2-yl)-1,3-dimethyl-1H-pyrazol-4-ylcarboxamide, N-(3'-chloro-4'-fluoro-5-fluorobiphenyl-2-yl)-1-methyl-3-difluoromethyl-1H-pyrazol-4-ylcarboxamide, N-(4'-fluoro-4-fluorobiphenyl-2-yl)-1-methyl-3-trifluoromethyl-1H-pyrazol-4-ylcarboxamide, N-(4'-fluoro-5-fluorobiphenyl-2-yl)-1-methyl-3-trifluoromethyl-1H-pyrazol-4-ylcarboxamide, N-(4'-chloro-5-fluorobiphenyl-2-yl)-1-methyl-3-trifluoromethyl-1H-pyrazol-4-ylcarboxamide, N-(4'-methyl-5-fluorobiphenyl-2-yl)-1-methyl-3-trifluoromethyl-1H-pyrazol-4-ylcarboxamide, N-(4'-fluoro-5-fluorobiphenyl-2-yl)-1,3-dimethyl-1H-pyrazol-4-ylcarboxamide, N-(4'-chloro-5-fluorobiphenyl-2-yl)-1,3-dimethyl-1H-pyrazol-4-ylcarboxamide, N-(4'-methyl-5-fluorobiphenyl-2-yl)-1,3-dimethyl-1H-pyrazol-4-ylcarboxamide, N-(4'-fluoro-6-fluorobiphenyl-2-yl)-1-methyl-3-trifluoromethyl-1H-pyrazol-4-ylcarboxamide, N-[2-(1,1,2,3,3,3-hexafluoropropoxy)phenyl]-3-difluoromethyl-1-methyl-1H-pyrazol-4-ylcarboxamide, N-[4'-(trifluoromethylthio)biphenyl-2-yl]-3-difluoromethyl-1-methyl-1H-pyrazol-4-ylcarboxamide, N-[4'-(trifluoromethylthio)biphenyl-2-yl]-1-methyl-3-trifluoromethyl-1-methyl-1H-pyrazol-4-ylcarboxamide, 3-(difluoromethyl)-1-methyl-N-[1,2,3,4-tetrahydro-9-(1-methylethyl)-1,4-methanonaphthalen-5-yl]-1H-pyrazol-4-ylcarboxamide, N-(3'-chloro-5-fluorobiphenyl-2-yl)-3-(difluoromethyl)-1-methylpyrazol-4-ylcarboxamide, N-(4'-chloro-5-fluorobiphenyl-2-yl)-3-(difluoromethyl)-1-methylpyrazol-4-ylcarboxamide, N-(4'-chlorobiphenyl-2-yl)-3-(difluoromethyl)-1-methylpyrazol-4-ylcarboxamide, N-(4'-bromobiphenyl-2-yl)-3-(difluoromethyl)-1-methylpyrazol-4-ylcarboxamide, N-(4'-iodobiphenyl-2-yl)-3-(difluoromethyl)-1-methylpyrazol-4-ylcarboxamide, N-(3',5'-difluorobiphenyl-2-yl)-3-(difluoromethyl)-1-methylpyrazol-4-ylcarboxamide, N-(2-chloro-4-fluorophenyl)-3-(difluoromethyl)-1-methylpyrazol-4-ylcarboxamide, N-(2-bromo-4-fluorophenyl)-3-(difluoromethyl)-1-methylpyrazol-4-ylcarboxamide, N-(2-iodo-4-fluorophenyl)-3-(difluoromethyl)-1-methylpyrazol-4-ylcarboxamide or N-[2-(1,3-dimethylbutyl)phenyl]-1,3-dimethyl-5-fluoro-1H-pyrazol-4-ylcarboxamide.

7. The process according to claim 1, wherein the reaction of II with III is undertaken at a pressure of from 200 to 600 mbar.

8. The process according to claim 1, wherein the reaction of II with III is undertaken at from 20 to 120° C.

9. The process according to claim 1, wherein the molar ratio of II to III is from 0.9:1 to 1.1:1.

10. The process according to claim 1, wherein the starting material is an arylamine III which has been obtained by hydrogenating the corresponding nitroaryl.

* * * * *